US009616086B2

(12) United States Patent
Hong et al.

(10) Patent No.: US 9,616,086 B2
(45) Date of Patent: Apr. 11, 2017

(54) USE OF MICRORNA OR INHIBITORS THEREOF IN REGULATION OF LIPID METABOLISM

(71) Applicant: Institute of Medicinal Biotechnology, Chinese Academy of Medical Sciences, Beijing (CN)

(72) Inventors: Bin Hong, Beijing (CN); Li Wang, Beijing (CN); Xiaojian Jia, Beijing (CN); Huajun Jiang, Beijing (CN); Yu Du, Beijing (CN); Fan Yang, Beijing (CN); Shuyi Si, Beijing (CN)

(73) Assignee: Institute of Medicinal Biotechnology, Chinese Academy of Medical Sciences, Beijing (CN)

( * ) Notice: Subject to any disclaimer, the term of this patent is extended or adjusted under 35 U.S.C. 154(b) by 0 days.

(21) Appl. No.: 14/763,902

(22) PCT Filed: Jan. 26, 2014

(86) PCT No.: PCT/CN2014/071485
§ 371 (c)(1),
(2) Date: Nov. 3, 2015

(87) PCT Pub. No.: WO2014/117697
PCT Pub. Date: Aug. 7, 2014

(65) Prior Publication Data
US 2016/0089390 A1 Mar. 31, 2016

(30) Foreign Application Priority Data

Jan. 30, 2013 (CN) .......................... 2013 1 0035358

(51) Int. Cl.
| | | |
|---|---|---|
| C12N 15/11 | (2006.01) | |
| A61K 31/713 | (2006.01) | |
| C12Q 1/68 | (2006.01) | |
| A61K 31/7105 | (2006.01) | |
| C12N 15/113 | (2010.01) | |
| G01N 33/92 | (2006.01) | |

(52) U.S. Cl.
CPC ........ *A61K 31/713* (2013.01); *A61K 31/7105* (2013.01); *C12N 15/113* (2013.01); *C12Q 1/6883* (2013.01); *C12Q 1/6897* (2013.01); *G01N 33/92* (2013.01); *C12N 2310/113* (2013.01); *C12N 2310/141* (2013.01); *C12N 2320/30* (2013.01); *C12Q 2600/136* (2013.01); *C12Q 2600/158* (2013.01); *C12Q 2600/178* (2013.01); *G01N 2405/00* (2013.01); *G01N 2500/04* (2013.01); *G01N 2500/10* (2013.01); *G01N 2800/044* (2013.01)

(58) Field of Classification Search
CPC ...................... C12N 2310/14; C12N 2310/141
See application file for complete search history.

(56) References Cited

U.S. PATENT DOCUMENTS

| 9,243,250 B2* | 1/2016 | Yang ................... C12N 15/1138 |
| 2013/0059906 A1* | 3/2013 | Rao ..................... A61K 31/7088 514/44 R |
| 2013/0171649 A1* | 7/2013 | Mayr .................. C12Q 1/6883 435/6.12 |
| 2013/0337459 A1* | 12/2013 | Yang .................. C12N 15/1138 435/6.12 |
| 2014/0024551 A1* | 1/2014 | Mayr .................. C12Q 1/6883 506/9 |

FOREIGN PATENT DOCUMENTS

| CN | 102031255 A | 4/2011 |
| CN | 102140468 A | 8/2011 |
| WO | WO 2009/108866 A2 | 9/2009 |
| WO | WO2011/103345 A2 * | 8/2011 |

OTHER PUBLICATIONS

Bao et al. PLoS One 10:1-14, 2015.*
International Search Report (ISR) for PCT/CN2014/071485; I.A. fd: Jan. 26, 2014, mailed Mar. 27, 2014, from the State Intellectual Property Office, the P.R. China, Beijing, China.
International Preliminary Report on Patentability (IPRP), Chapter I of the Patent Cooperation Treaty, including the Written Opinion for PCT/CN2014/071485; I.A. fd: Jan. 26, 2014, issued Aug. 4, 2015, by the International Bureau of WIPO, Geneva, Switzerland.
Hu, Z et al., "MicroRNAs 125a and 455 repress lipoprotein-supported steroidogenesis by targeting scavenger receptor class B type I in steroidogenic cells," Mol Cell Biol, Dec. 2012, 32(24):5035-5045. doi: 10.1128/MCB.01002-12. Epub Oct. 8, 2012, American Society for Microbiology, Washington, DC.
Wang, L et al.,"MicroRNAs 185, 96, and 223 repress selective high-density lipoprotein cholesterol uptake through post-transcriptional inhibition," Mol Cell Biol, May 2013, 33(10):1956-1964. doi: 10.1128/MCB.01580-12. Epub Mar. 4, 2013, American Society for Microbiology, Washington, DC.

* cited by examiner

*Primary Examiner* — Brian Whiteman
(74) *Attorney, Agent, or Firm* — Sterne, Kessler, Goldstein & Fox P.L.L.C.

(57) ABSTRACT

The present invention relates to use of a microRNA or an inhibitor thereof, and specifically, the present invention relates to use of a microRNA or an inhibitor thereof in preparing a medicament for regulating lipid metabolism or preparing a medicament for preventing or treating a disease related to lipid metabolism. The microRNA is one or more of the following: miRNA-96, miRNA-185, and miRNA-223. The present invention also relates to use of the microRNA or the inhibitor thereof in regulating the expression level of a protein related to lipid metabolism. The present invention also relates to a composition comprising the microRNA or the inhibitor thereof. The microRNA or the inhibitor thereof in the present invention can be used as a pharmaceutical component, and can be applied in preventing or treating a disease caused by lipid metabolism disorders such as hyperlipidemia, atherosclerosis, coronary heart disease or other diseases.

7 Claims, 8 Drawing Sheets

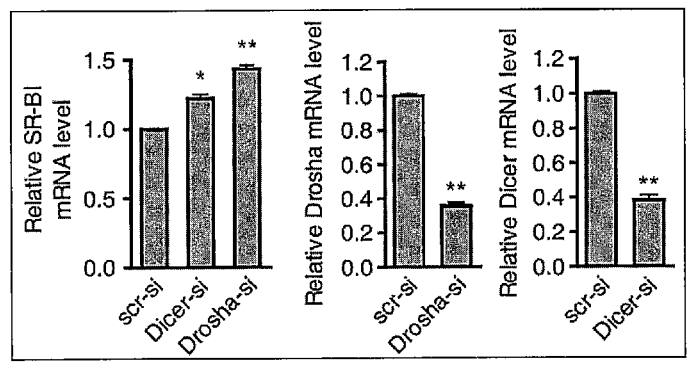

Fig. 1

| | | | |
|---|---|---|---|
| SEQ ID NO: 2 | 3' aguCCUUGACGGAAAGAGAGGu 5'   hsa-miR-185 | 3' aguccuugacggaaaGAGAGGu 5'   hsa-miR-185 | SEQ ID NO: 2 |
| SEQ ID NO: 8 | 265: 5' ucuGGAACCUUCUCUCCa 3'   SR-BI 3'UTR | 69: 5' cccgcuucucccggaCUCUCCc 3'   SR-BI 3'UTR | SEQ ID NO: 9 |
| SEQ ID NO: 1 | 3' ucguuuuuacACGAUCACGGUUu 5'   hsa-miR-96 | 3' accccauaaacuGUUUGACUGu 5'   hsa-miR-223 | SEQ ID NO: 3 |
| SEQ ID NO: 10 | 447: 5' agugccgccuUCCUGUGCCAAu 3'   SR-BI 3'UTR | 681: 5' uuuccuccagccUAAACUGACa 3'   SR-BI 3'UTR | SEQ ID NO: 11 |

Fig. 2

| | hsa-miR-96 Site (461-467) | hsa-miR-223 Site (694-701) | |
|---|---|---|---|
| SEQ ID NO: 12 | Hsa CCUGUGCCAAAU | Hsa AGCCUAAACUGACAUCAUC | SEQ ID NO: 16 |
| | Ptr CCUGUGCCAAAU | Ptr AGCCUAAACUGACAUCAUC | |
| | Mml CCUGUGCCAAAU | Mml AGCCUAAACUGACAUCAUC | |
| SEQ ID NO: 13 | Cfa CUUGUGCCAAAG | Bta AGCCUAAACUGACAUCAUC | |
| SEQ ID NO: 14 | Fca CUCGUGCCAAAG | Eca AGC--UAAACUGACAUCAUC | SEQ ID NO: 17 |
| SEQ ID NO: 13 | Eca CUUGUGCCAAAG | Cfa AGCCUAAACUGACAUCUUC | SEQ ID NO: 18 |
| SEQ ID NO: 15 | Mmu CUUGUGCCAAGG | Ete AGUUGAAACUGACUUCAUC | SEQ ID NO: 19 |
| | | Ssc AGCCUAAACUGACAGCAUC | SEQ ID NO: 20 |
| | | Ocu AGCCUAAACUGACAUCAGC | SEQ ID NO: 21 |

| | hsa-miR-185 Site1 (84-89) | hsa-miR-185 Site2 (274-281) | |
|---|---|---|---|
| | Hsa GACUCUCCCAG | Hsa CUUCUCUCCACG | |
| SEQ ID NO: 22 | Ptr GACUCUCCCAG | Ptr CUUCUCUCCACG | SEQ ID NO: 24 |
| | Mml GACUCUCCCAG | Mml CUUCUCUCCACG | |
| SEQ ID NO: 23 | Rno GACUCUCUCAG | Cpo CUUCUCUCCAAG | SEQ ID NO: 25 |
| | Mmu GACUCUCUCAG | Mmu CUU--UCUCCAUC | SEQ ID NO: 26 |

Fig. 3

|  | *hsa-miR-96 Site (497-505)* |  | *hsa-miR-223 Site (3137-3145)* |  |
|---|---|---|---|---|
| SEQ ID NO: 33 | Ame ATTACTAGTGCCAAGTC | Mmu | TTGCAAAACTAGACAAAAG | |
| SEQ ID NO: 34 | Mmu GTTACTAGTGCCAAGTT | Ptr | TTGCAAAACTAGACAAAAG | SEQ ID NO: 37 |
| SEQ ID NO: 35 | Ptr GTTATTAGTGCCAAGTT | Hsa | TTGCAAAACTAGACAAAAG | |
| | Hsa GTTATTAGTGCCAAGTT | | | |
| SEQ ID NO: 36 | Pab ATTATTAGTGCCAAGTT | | | |

Fig. 9

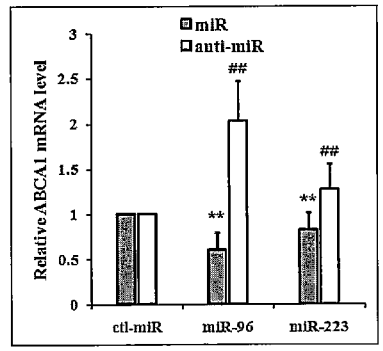

Fig. 10

| SEQ ID NO: 2 | 3' aguccUUGACGGAAAGAGAGGu 5' hsa-miR-185 | 3' agUCCUU - - - GACGGAAAGAGAGGu 5' hsa-miR-185 | SEQ ID NO: 2 |
|---|---|---|---|
| | ‖‖‖‖‖ | ‖‖‖‖‖ | |
| SEQ ID NO: 38 | 235: 5' augacACCUCCAUUUCUCUCCa 3' LDLR 3'UTR | 254: 5' ccAGGAAGUUUUGAGUUUCUCUCCa 3' LDLR 3'UTR | SEQ ID NO: 39 |

Fig. 11

|  | *hsa-miR-185 Site 1 (250-255)*   *hsa-miR-185 Site 2 (272-277)* |
|---|---|
| SEQ ID NO: 40 | Hsa GGACCAGGATGACACCTCCATTTCTCTCCAGGAAGTTTTGAGTTTCTCTCCACCGTGA |
| | Ptr GGACCAGGATGACACCTCCATTTCTCTCCAGGAAGTTTTGAGTTTCTCTCCACCGTGA |
| SEQ ID NO: 41 | Pab GGGCCAGGATGACACCTCCATTTCTCTCCAGGAAGTTTTGAGTTTCTCTCCACCGTGA |
| SEQ ID NO: 42 | Bta AATCTG----------------------TCCTCTCCGGGAATCTCTGAGCTGCTCTCCTTCTAGA |

Fig. 12

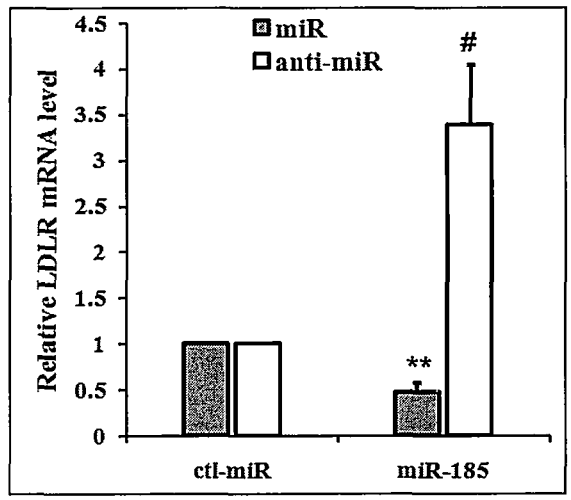
Fig. 13
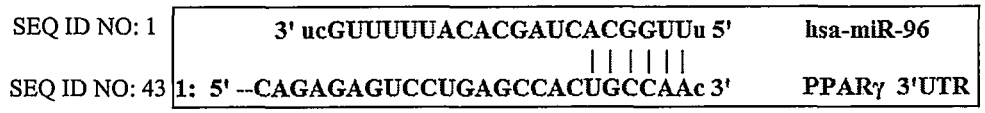
Fig. 14
|  |  | hsa-miR-96 Site (19-24) |
|---|---|---|
| SEQ ID NO: 44 | Bta | TTCACTGACAGCATCTT |
| SEQ ID NO: 45 | Ssc | TTCACCGACAACATTCT |
| SEQ ID NO: 46 | Mmu | CCCGCTGACAACGTGTT |
| SEQ ID NO: 47 | Rno | GTCGCTGACAAAGTGTT |
| SEQ ID NO: 48 | Hsa | GCCACTGCCAACATTTC |
|  | Ptr | GCCACTGCCAACATTTC |
| SEQ ID NO: 49 | Gga | TCCTCTGACATAATGTA |
| SEQ ID NO: 50 | Fca | TTCACTGACAACGTTTT |
| SEQ ID NO: 51 | Pab | GCCGCTGCCAACATTTC |
Fig. 15

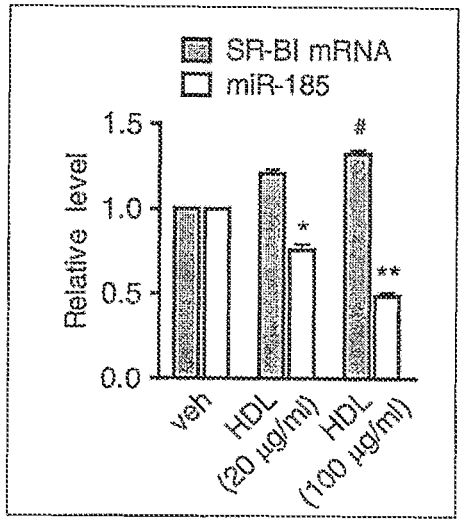
Fig. 19
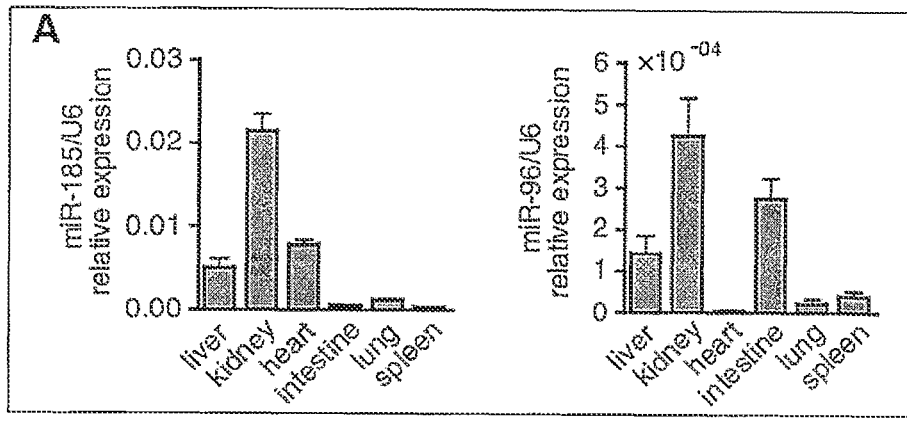
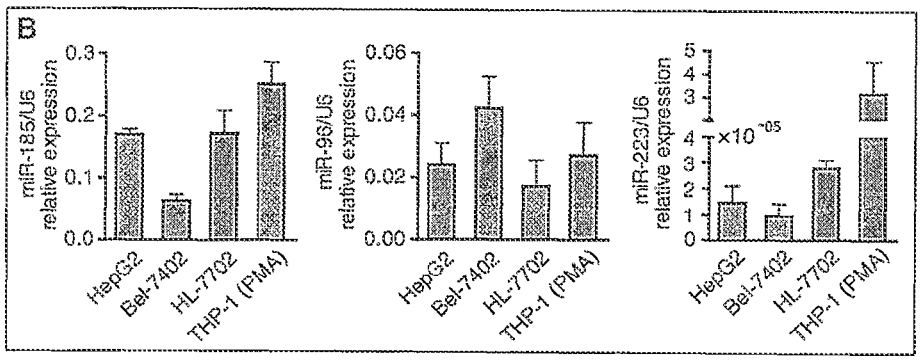
Fig. 20

… (1 / 2) …

SEQUENCE LISTING

<160> NUMBER OF SEQ ID NOS: 51

<210> SEQ ID NO 1
<211> LENGTH: 23
<212> TYPE: RNA
<213> ORGANISM: artificial sequence
<220> FEATURE:
<223> OTHER INFORMATION: synthetically created RNA

<400> SEQUENCE: 1
uuuggcacua gcacauuuuu gcu        23

<210> SEQ ID NO 2
<211> LENGTH: 22
<212> TYPE: RNA
<213> ORGANISM: artificial sequence
<220> FEATURE:
<223> OTHER INFORMATION: synthetically created RNA

<400> SEQUENCE: 2
uggagagaaa ggcaguuccu ga         22

<210> SEQ ID NO 3
<211> LENGTH: 22
<212> TYPE: RNA
<213> ORGANISM: artificial sequence
<220> FEATURE:
<223> OTHER INFORMATION: synthetically created RNA

<400> SEQUENCE: 3
ugucaguuug ucaaauaccc ca         22

<210> SEQ ID NO 4
<211> LENGTH: 23
<212> TYPE: RNA
<213> ORGANISM: artificial sequence
<220> FEATURE:
<223> OTHER INFORMATION: synthetically created RNA

<400> SEQUENCE: 4
agcaaaaaug ugcuagugcc aaa        23

<210> SEQ ID NO 5
<211> LENGTH: 22
<212> TYPE: RNA
<213> ORGANISM: artificial sequence
<220> FEATURE:
<223> OTHER INFORMATION: synthetically created RNA

<400> SEQUENCE: 5
ucaggaacug ccuuucucuc ca         22

<210> SEQ ID NO 6
<211> LENGTH: 22
<212> TYPE: RNA
<213> ORGANISM: artificial sequence
<220> FEATURE:
<223> OTHER INFORMATION: synthetically created RNA

<400> SEQUENCE: 6
ugggguauuu gacaaacuga ca         22

<210> SEQ ID NO 7
<211> LENGTH: 22
<212> TYPE: RNA
<213> ORGANISM: artificial sequence

```
<220> FEATURE:
<223> OTHER INFORMATION: synthetically created RNA

<400> SEQUENCE: 7
uggaauguaa agaaguaugu au                                              22

<210> SEQ ID NO 8
<211> LENGTH: 18
<212> TYPE: RNA
<213> ORGANISM: Artificial Sequence
<220> FEATURE:
<223> OTHER INFORMATION: 265 SR-BI 3'UTR

<400> SEQUENCE: 8
ucuggaaccu ucucucca                                                   18

<210> SEQ ID NO 9
<211> LENGTH: 22
<212> TYPE: RNA
<213> ORGANISM: Artificial Sequence
<220> FEATURE:
<223> OTHER INFORMATION: 69 SR-BI 3'UTR

<400> SEQUENCE: 9
cccgcuucuc ccggacucuc cc                                              22

<210> SEQ ID NO 10
<211> LENGTH: 22
<212> TYPE: RNA
<213> ORGANISM: Artificial Sequence
<220> FEATURE:
<223> OTHER INFORMATION: 447 SR-BI 3'UTR

<400> SEQUENCE: 10
agugccgccu uccugugcca aa                                              22

<210> SEQ ID NO 11
<211> LENGTH: 22
<212> TYPE: RNA
<213> ORGANISM: Artificial Sequence
<220> FEATURE:
<223> OTHER INFORMATION: 681 SR-BI 3'UTR

<400> SEQUENCE: 11
uuuccuccag ccuaaacuga ca                                              22

<210> SEQ ID NO 12
<211> LENGTH: 12
<212> TYPE: RNA
<213> ORGANISM: Artificial Sequence
<220> FEATURE:
<223> OTHER INFORMATION: hsa-miR-96 Site (461-467) Hsa, Ptr, Mml

<400> SEQUENCE: 12
ccugugccaa au                                                         12

<210> SEQ ID NO 13
<211> LENGTH: 12
<212> TYPE: RNA
<213> ORGANISM: Artificial Sequence
<220> FEATURE:
<223> OTHER INFORMATION: hsa-miR-96 Site (461-467) Cfa, Eca

<400> SEQUENCE: 13
cuugugccaa ag                                                         12
```

```
<210> SEQ ID NO 14
<211> LENGTH: 12
<212> TYPE: RNA
<213> ORGANISM: Artificial Sequence
<220> FEATURE:
<223> OTHER INFORMATION: hsa-miR-96 Site (461-467) Fca

<400> SEQUENCE: 14
cucgugccaa ag                                                              12

<210> SEQ ID NO 15
<211> LENGTH: 12
<212> TYPE: RNA
<213> ORGANISM: Artificial Sequence
<220> FEATURE:
<223> OTHER INFORMATION: hsa-miR-96 Site (461-467) Mmu

<400> SEQUENCE: 15
cuugugccaa gg                                                              12

<210> SEQ ID NO 16
<211> LENGTH: 19
<212> TYPE: RNA
<213> ORGANISM: Artificial Sequence
<220> FEATURE:
<223> OTHER INFORMATION: hsa-miR-223 Site (694-701) Hsa, Ptr, Mml, Bta

<400> SEQUENCE: 16
agccuaaacu gacaucauc                                                       19

<210> SEQ ID NO 17
<211> LENGTH: 18
<212> TYPE: RNA
<213> ORGANISM: Artificial Sequence
<220> FEATURE:
<223> OTHER INFORMATION: hsa-miR-223 Site (694-701) Eca

<400> SEQUENCE: 17
agcuaaacug acaucauc                                                        18

<210> SEQ ID NO 18
<211> LENGTH: 19
<212> TYPE: RNA
<213> ORGANISM: Artificial Sequence
<220> FEATURE:
<223> OTHER INFORMATION: hsa-miR-223 Site (694-701) Cfa

<400> SEQUENCE: 18
agccuaaacu gacaucuuc                                                       19

<210> SEQ ID NO 19
<211> LENGTH: 19
<212> TYPE: RNA
<213> ORGANISM: Artificial Sequence
<220> FEATURE:
<223> OTHER INFORMATION: hsa-miR-223 Site (694-701) Ete

<400> SEQUENCE: 19
aguugaaacu gacuucauc                                                       19

<210> SEQ ID NO 20
<211> LENGTH: 19
<212> TYPE: RNA
<213> ORGANISM: Artificial Sequence
<220> FEATURE:
<223> OTHER INFORMATION: hsa-miR-223 Site (694-701) Ssc
```

```
<400> SEQUENCE: 20
agccuaaacu gacagcauc                                            19

<210> SEQ ID NO 21
<211> LENGTH: 19
<212> TYPE: RNA
<213> ORGANISM: Artificial Sequence
<220> FEATURE:
<223> OTHER INFORMATION: hsa-miR-223 Site (694-701) Ocu

<400> SEQUENCE: 21
agccuaaacu gacaucagc                                            19

<210> SEQ ID NO 22
<211> LENGTH: 11
<212> TYPE: RNA
<213> ORGANISM: Artificial Sequence
<220> FEATURE:
<223> OTHER INFORMATION: hsa-miR-185 Site1 (84-89) Hsa, Ptr, Mml

<400> SEQUENCE: 22
gacucuccca g                                                    11

<210> SEQ ID NO 23
<211> LENGTH: 11
<212> TYPE: RNA
<213> ORGANISM: Artificial Sequence
<220> FEATURE:
<223> OTHER INFORMATION: hsa-miR-185 Site1 (84-89) Rno, Mmu

<400> SEQUENCE: 23
gacucucuca g                                                    11

<210> SEQ ID NO 24
<211> LENGTH: 12
<212> TYPE: RNA
<213> ORGANISM: Artificial Sequence
<220> FEATURE:
<223> OTHER INFORMATION: hsa-miR-185 Site2 (274-281) Hsa, Ptr, Mml

<400> SEQUENCE: 24
cuucucucca cg                                                   12

<210> SEQ ID NO 25
<211> LENGTH: 12
<212> TYPE: RNA
<213> ORGANISM: Artificial Sequence
<220> FEATURE:
<223> OTHER INFORMATION: hsa-miR-185 Site2 (274-281) Cpo

<400> SEQUENCE: 25
cuucucucca ag                                                   12

<210> SEQ ID NO 26
<211> LENGTH: 11
<212> TYPE: RNA
<213> ORGANISM: Artificial Sequence
<220> FEATURE:
<223> OTHER INFORMATION: hsa-miR-185 Site2 (274-281) Mmu

<400> SEQUENCE: 26
cuuucuccau c                                                    11

<210> SEQ ID NO 27
```

```
<210> SEQ ID NO 27
<211> LENGTH: 17
<212> TYPE: DNA
<213> ORGANISM: Artificial Sequence
<220> FEATURE:
<223> OTHER INFORMATION: SR-BI 3'UTR (DEL1)

<400> SEQUENCE: 27
cccgcttctc ccggaca                                                      17

<210> SEQ ID NO 28
<211> LENGTH: 23
<212> TYPE: DNA
<213> ORGANISM: Artificial Sequence
<220> FEATURE:
<223> OTHER INFORMATION: SR-B1 3'UTR (WT1)

<400> SEQUENCE: 28
cccgcttctc ccggactctc cca                                               23

<210> SEQ ID NO 29
<211> LENGTH: 15
<212> TYPE: DNA
<213> ORGANISM: Artificial Sequence
<220> FEATURE:
<223> OTHER INFORMATION: SR-BI 3'UTR (DEL2)

<400> SEQUENCE: 29
ctgttctgga acctc                                                        15

<210> SEQ ID NO 30
<211> LENGTH: 23
<212> TYPE: DNA
<213> ORGANISM: Artificial Sequence
<220> FEATURE:
<223> OTHER INFORMATION: SR-B1 3'UTR (WT2)

<400> SEQUENCE: 30
ctgttctgga accttctctc cac                                               23

<210> SEQ ID NO 31
<211> LENGTH: 22
<212> TYPE: RNA
<213> ORGANISM: Artificial Sequence
<220> FEATURE:
<223> OTHER INFORMATION: 485 ABCA1 3'UTR

<400> SEQUENCE: 31
ugccagaguu auuagugcca ag                                                22

<210> SEQ ID NO 32
<211> LENGTH: 23
<212> TYPE: RNA
<213> ORGANISM: Artificial Sequence
<220> FEATURE:
<223> OTHER INFORMATION: 3124 ABCA1 3'UTR

<400> SEQUENCE: 32
ucugagaauu gcaaaacuag aca                                               23

<210> SEQ ID NO 33
<211> LENGTH: 17
<212> TYPE: DNA
<213> ORGANISM: Artificial Sequence
<220> FEATURE:
<223> OTHER INFORMATION: hsa-miR-96 Site (497-505) Ame

<400> SEQUENCE: 33
```

```
attactagtg ccaagtc                                                17

<210> SEQ ID NO 34
<211> LENGTH: 17
<212> TYPE: DNA
<213> ORGANISM: Artificial Sequence
<220> FEATURE:
<223> OTHER INFORMATION: hsa-miR-96 Site (497-505) Mmu

<400> SEQUENCE: 34
gttactagtg ccaagtt                                                17

<210> SEQ ID NO 35
<211> LENGTH: 17
<212> TYPE: DNA
<213> ORGANISM: Artificial Sequence
<220> FEATURE:
<223> OTHER INFORMATION: hsa-miR-96 Site (497-505) Ptr, Hsa

<400> SEQUENCE: 35
gttattagtg ccaagtt                                                17

<210> SEQ ID NO 36
<211> LENGTH: 17
<212> TYPE: DNA
<213> ORGANISM: Artificial Sequence
<220> FEATURE:
<223> OTHER INFORMATION: hsa-miR-96 Site (497-505) Pab

<400> SEQUENCE: 36
attattagtg ccaagtt                                                17

<210> SEQ ID NO 37
<211> LENGTH: 19
<212> TYPE: DNA
<213> ORGANISM: Artificial Sequence
<220> FEATURE:
<223> OTHER INFORMATION: hsa-miR-223 Site (3137-3145) Mmu, Ptr, Hsa

<400> SEQUENCE: 37
ttgcaaaact agacaaaag                                              19

<210> SEQ ID NO 38
<211> LENGTH: 22
<212> TYPE: RNA
<213> ORGANISM: Artificial Sequence
<220> FEATURE:
<223> OTHER INFORMATION: 235 LDLR 3'UTR

<400> SEQUENCE: 38
augacaccuc cauuucucuc ca                                          22

<210> SEQ ID NO 39
<211> LENGTH: 25
<212> TYPE: RNA
<213> ORGANISM: Artificial Sequence
<220> FEATURE:
<223> OTHER INFORMATION: 254 LDLR 3'UTR

<400> SEQUENCE: 39
ccaggaaguu uugaguuucu cucca                                       25

<210> SEQ ID NO 40
<211> LENGTH: 58
<212> TYPE: DNA
```

```
<213> ORGANISM: Artificial Sequence
<220> FEATURE:
<223> OTHER INFORMATION: hsa-miR-185 Site 1 (250-255) and hsa-miR-185
      Site 2 (272-277) Hsa, Ptr

<400> SEQUENCE: 40
ggaccaggat gacacctcca tttctctcca ggaagttttg agtttctctc caccgtga        58

<210> SEQ ID NO 41
<211> LENGTH: 58
<212> TYPE: DNA
<213> ORGANISM: Artificial Sequence
<220> FEATURE:
<223> OTHER INFORMATION: hsa-miR-185 Site 1 (250-255) and hsa-miR-185
      Site 2 (272-277) Pab

<400> SEQUENCE: 41
gggccaggat gacacctcca tttctctcca ggaagttttg agtttctctc caccgtga        58

<210> SEQ ID NO 42
<211> LENGTH: 43
<212> TYPE: DNA
<213> ORGANISM: Artificial Sequence
<220> FEATURE:
<223> OTHER INFORMATION: hsa-miR-185 Site 1 (250-255) and hsa-miR-185
      Site 2 (272-277) Bta

<400> SEQUENCE: 42
aatctgtcct ctccgggaat ctctgagctg ctctccttct aga                       43

<210> SEQ ID NO 43
<211> LENGTH: 25
<212> TYPE: RNA
<213> ORGANISM: Artificial Sequence
<220> FEATURE:
<223> OTHER INFORMATION: 1 PPAR-gamma 3'UTR

<400> SEQUENCE: 43
cagagagucc ugagccacug ccaac                                           25

<210> SEQ ID NO 44
<211> LENGTH: 17
<212> TYPE: DNA
<213> ORGANISM: Artificial Sequence
<220> FEATURE:
<223> OTHER INFORMATION: hsa-miR-96 Site (19-24) Bta

<400> SEQUENCE: 44
ttcactgaca gcatctt                                                    17

<210> SEQ ID NO 45
<211> LENGTH: 17
<212> TYPE: DNA
<213> ORGANISM: Artificial Sequence
<220> FEATURE:
<223> OTHER INFORMATION: hsa-miR-96 Site (19-24) Ssc

<400> SEQUENCE: 45
ttcaccgaca acattct                                                    17

<210> SEQ ID NO 46
<211> LENGTH: 17
<212> TYPE: DNA
<213> ORGANISM: Artificial Sequence
<220> FEATURE:
<223> OTHER INFORMATION: hsa-miR-96 Site (19-24) Mmu
```

```
<400> SEQUENCE: 46
cccgctgaca acgtgtt                                                  17

<210> SEQ ID NO 47
<211> LENGTH: 17
<212> TYPE: DNA
<213> ORGANISM: Artificial Sequence
<220> FEATURE:
<223> OTHER INFORMATION: hsa-miR-96 Site (19-24) Rno

<400> SEQUENCE: 47
gtcgctgaca aagtgtt                                                  17

<210> SEQ ID NO 48
<211> LENGTH: 17
<212> TYPE: DNA
<213> ORGANISM: Artificial Sequence
<220> FEATURE:
<223> OTHER INFORMATION: hsa-miR-96 Site (19-24) Hsa, Ptr

<400> SEQUENCE: 48
gccactgcca acatttc                                                  17

<210> SEQ ID NO 49
<211> LENGTH: 17
<212> TYPE: DNA
<213> ORGANISM: Artificial Sequence
<220> FEATURE:
<223> OTHER INFORMATION: hsa-miR-96 Site (19-24) Gga

<400> SEQUENCE: 49
tcctctgaca taatgta                                                  17

<210> SEQ ID NO 50
<211> LENGTH: 17
<212> TYPE: DNA
<213> ORGANISM: Artificial Sequence
<220> FEATURE:
<223> OTHER INFORMATION: hsa-miR-96 Site (19-24) Fca

<400> SEQUENCE: 50
ttcactgaca acgtttt                                                  17

<210> SEQ ID NO 51
<211> LENGTH: 17
<212> TYPE: DNA
<213> ORGANISM: Artificial Sequence
<220> FEATURE:
<223> OTHER INFORMATION: hsa-miR-96 Site (19-24) Pab

<400> SEQUENCE: 51
gccgctgcca acatttc                                                  17
```

USE OF MICRORNA OR INHIBITORS THEREOF IN REGULATION OF LIPID METABOLISM

REFERENCE TO SEQUENCE LISTING SUBMITTED ELECTRONICALLY

The content of the electronically submitted substitute sequence listing, file name 3173_0020001_SeqListing.txt, size 10,722 bytes; and date of creation Nov. 1, 2016, filed herewith, is incorporated herein by reference in its entirety.

TECHNICAL FIELD

The present invention relates to use of a microRNA or an inhibitor thereof, and specifically to use of a microRNA or an inhibitor thereof in preparing a medicament for regulating lipid metabolism or in preparing a medicament for preventing or treating a disease related to lipid metabolism. Furthermore, a microRNA or an inhibitor thereof can be used as a tool drug for studying the above related disease or functional mechanisms of related proteins. The present invention also relates to use of a microRNA or an inhibitor thereof in regulating the expression level of the protein related to lipid metabolism. The present invention also relates to a composition comprising a microRNA or an antisense oligonucleotide inhibitor thereof.

BACKGROUND

Atherosclerotic cardiovascular and cerebrovascular disease is the primary disease causing disability and death in the world, and dyslipidemia is one of the most important risk factors for atherosclerosis. It is a long-term research task for medical workers to find a medicament with a significant effect and a reliable safety for controlling serum lipid.

A large number of epidemiological studies have found that the morbidity and mortality of cardiovascular diseases such as atherosclerosis and coronary heart disease are negatively correlated with the level of plasma high-density lipoprotein cholesterol (HDL-C) and are positively correlated with the level of plasma low-density lipoprotein cholesterol (LDL-C). With the increase of HDL-C concentration by 0.026 mM, the risk of cardiovascular event reduces by 2-3%; and with the decrease of HDL-C concentration by 2-3 mM, the risk of cardiovascular event reduces by about 40-50%. The anti-atherosclerosis function of plasma high-density lipoprotein is achieved mainly through the reverse cholesterol transport (RCT) mediated by plasma high-density lipoprotein. The more quickly HDL-C is cleared away, the more efficiently cholesterol is reversely transported, and the lower the morbidity and mortality risks of atherosclerosis are. In addition, the protective effects of HDL on the cardiovascular system are also relevant to its anti-inflammatory activity and antioxidant activity.

The human scavenger receptor class B, member 1 (SR-BI), which is also known as CD36 and lysosomal integral membrane protein-II analogous-1 (CLA-1), is an important integral membrane glycoprotein of scavenger receptor family. Experiments have shown that SR-BI is a key molecule involved in selective uptake of HDL related cholesterol esters in hepatocytes in mice. As a functional high-density lipoprotein receptor with high expression in liver, SR-BI binds with HDL with high affinity and high saturation to mediate the selective uptake of HDL-C, which is the final speed limiting step in RCT. The overexpression of hepatic SR-BI promotes the reverse transportation of HDL-C, enhances the clearance of plasma HDL and reduces the morbidity and mortality risks of clinical atherosclerosis and associated cardiovascular diseases.

ATP-binding cassette transporter A1 (ATP-binding cassette, sub-family A, member 1. ABCA1) is a membrane-associated protein for transporting various substrates using ATP as energy. The function of ABCA1 is the most prominent in macrophages and hepatocytes, wherein it functions as an efflux pump in the process of intracellular lipid clearance by using cholesterol as a substrate. Mutation of ABCA1 gene is closely related to Tangier disease and familial HDL deficiency. Oxidized lipoprotein cholesterol uptaken by macrophage undergoes efflux through ABCA1 as free cholesterols, then forms pre-β-HDL by binding to lipid-poor apoA-1. This process is the first rate-limiting step in RCT and has significant effects on lipid metabolism and the occurrence/development of atherosclerosis.

The main function of low density lipoprotein receptor (LDLR) is to uptake cholesterols into cells, and the uptaken cholesterols are used for cell proliferation and synthesis of steroid hormones and bile acid salts. LDL or other lipoproteins containing ApoB100 and ApoE such as VLDL, β-VLDL are internalized into cells by binding to LDL receptor, which enables the cell to obtain lipid, mainly cholesterol. Such metabolism pathway is known as LDL receptor pathway, which depends on membranal pinocytosis mediated by LDL receptor. Mutation of LDLR gene will cause autosomal dominant genetic disease and familial hypercholesterolemia.

Peroxisome proliferator-activated receptors γ (PPAR-γ or PPARG) form heterodimers with retinoid X receptors (RXRs) to regulate transcription of various genes. PPAR-γ has an important regulatory effect on adipocyte differentiation. In addition, PPAR-γ is also closely associated with many pathological processes, such as obesity, diabetes, atherosclerosis and cancer. Recent studies have shown that PPAR-γ regulates and intervenes the balance of cholesterol and lipid in macrophages, thus affecting the progress of atherosclerosis. The regulatory process is associated with various lipoprotein receptors. Studies have shown that PPAR-γ may inhibit expression of scavenger receptor A (SR-A) by inhibiting activity of transcription factor activation protein-1 (AP-1), thus resulting in the decrease of the lipoprotein uptake ability of macrophages. In differentiated macrophages, PPAR-γ ligand also induces SR-BI expression and promotes cholesterol efflux from foam cells. Another study suggests that PPAR-γ may also stimulate critical steps in reverse cholesterol transport by inducing ABCA1 and SR-BI, thereby promoting cholesterol efflux.

MicroRNA (miRNA, miR) is a highly-conserved, single-strand and non-coding small RNA, and consists of about 20-22 single nucleotides. MicroRNA is widely found in eukaryotes and involved in post transcriptional regulation and translational regulation. MicroRNA plays an important role in eukaryotic gene regulation and is widely involved in basic life activities, such as cell proliferation, differentiation, development, metabolism, apoptosis and the like. MicroRNA is highly-conserved, timing, and tissue-specific. Through incompletely complementary binding with target genes, each microRNA has the potential of regulating multiple mRNAs. The stability of the expression level of microRNA is essential to the normal physiologic function in organism and the maintaining of dynamic balance of metabolism.

Recent studies have shown that, in addition to their regulatory effect on normal physiological process, microRNAs are important in many pathological processes such as tumors, glycometabolism and lipid metabolism diseases, and may play important roles in diagnosis and treatment of diseases. MicroRNA plays an important role in regulating the development of cardiovascular system and its pathological process. Highly specific microRNA expression patterns occur in case of cardiovascular disease, such as cardiac hypertrophy, heart failure, post myocardial infarction remodeling and vascular remodeling. Under different pathological conditions, the expression profiles of microRNA are different. Under various diseases such as tumors and cardiovascular diseases, specific microRNAs with differential expression can serve as biological markers for diagnosis and typing of various diseases. Databases of diseases related to microRNA have been established. The studies on the correlations between cellular targets of microRNA and the phenotypes of cardiovascular disease demonstrated new biological pathways and pathological mechanisms.

An increase or decrease in microRNA expression level can cause severe pathological consequence, indicating that stabilization of microRNA expression level in target organs may become a new way for the treatment of diseases. Endogenous microRNA abundance can be changed by oligonucleotide inhibitors or microRNA in vivo, so that single or multiple microRNA levels are artificially controlled, thereby enabling treatment strategies based on microRNA to be applied in clinic. If these methods can be safely and effectively applied to human, it will greatly contribute to treatments of critical diseases such as cardiovascular and cerebrovascular diseases.

Contents of the Invention

In present invention, mRNA level of SR-BI gene, a key molecule in the process of reverse cholesterol transport, is significantly up-regulated by inhibiting expressions of Dicer and Drosha, which are two key enzymes during generation of microRNA, by using gene silencing with siRNA. This suggests that microRNA plays an important role in the regulation of SR-BI expression. Through screening and testing the roles of predicted miRNAs, three miRNAs including microRNA-96 (miR-96), microRNA-185 (miR-185) and microRNA-223 (miR-223) which are capable of significantly reducing the mRNA level of SR-BI gene in hepatic cell are obtained eventually. The biological activities of the three microRNAs are further detected, and the regulatory effect of the three microRNAs or inhibitors thereof on lipid metabolism-related proteins are confirmed. The invention is on the basis of these findings.

One aspect of the invention relates to use of an inhibitor of microRNA (miRNA) in preparing a medicament for regulating lipid metabolism, wherein the microRNA is one or two or three selected from the group consisting of miRNA-96, miRNA-185, and miRNA-223.

Another aspect of the invention relates to use of an inhibitor of microRNA in preparing a medicament for preventing or treating a disease related to lipid metabolism, wherein the microRNA is one or two or three selected from the group consisting of miRNA-96, miRNA-185, and miRNA-223, and the disease related to lipid metabolism is, for example, hyperlipidemia caused by lipid metabolism disorders (especially hypercholesterolemia, hypertriglyceridemia and the like), atherosclerosis, cardiovascular and cerebrovascular diseases (especially coronary heart disease, myocardial infarction, stroke and the like), Alzheimer's disease, obesity, diabetes or metabolic syndrome and the like.

Another aspect of the invention relates to a composition comprising an inhibitor of microRNA, wherein the microRNA is one or two or three selected from the group consisting of miRNA-96, miRNA-185, and miRNA-223, and the composition is used for regulating lipid metabolism or preventing or treating a disease related to lipid metabolism, wherein the disease related to lipid metabolism is, for example, hyperlipidemia caused by lipid metabolism disorders (especially hypercholesterolemia, hypertriglyceridemia and the like), atherosclerosis, cardiovascular and cerebrovascular diseases (especially coronary heart disease, myocardial infarction, stroke and the like), Alzheimer's disease, obesity, diabetes or metabolic syndrome and the like.

Another aspect of the invention relates to use of a microRNA in down-regulating the expression level of human scavenger receptor class B, type I (SR-BI) in cells (e.g. in vitro or in vivo), wherein the microRNA is one or two or three selected from the group consisting of miRNA-96, miRNA-185, and miRNA-223.

Another aspect of the invention relates to use of an inhibitor of microRNA in up-regulating the expression level of human scavenger receptor class B, type I in cells (e.g. in vitro or in vivo), or in manufacturing a preparation for up-regulating the expression level of human scavenger receptor class B, type I in cells (e.g. in vitro or in vivo), wherein the microRNA is one or two or three selected from the group consisting of miRNA-96, miRNA-185, and miRNA-223.

Another aspect of the invention relates to use of miRNA-96 and/or miRNA-223 in down-regulating the expression level of ATP-binding cassette transporter A1 (ABCA1) in cells (e.g. in vitro or in vivo).

Another aspect of the invention relates to use of inhibitors of miRNA-96 and/or miRNA-223 in up-regulating the expression level of ATP-binding cassette transporter A1 (ABCA1) in cells (e.g. in vitro or in vivo), or in manufacturing a preparation for up-regulating the expression level of ATP-binding cassette transporter A1 in cells.

Another aspect of the invention relates to use of miRNA-185 in down-regulating the expression level of low-density lipoprotein receptor in cells (e.g. in vitro or in vivo).

Another aspect of the invention relates to use of an inhibitor of miRNA-185 in up-regulating the expression level of low-density lipoprotein receptor in cells (e.g. in vitro or in vivo), or in manufacturing a preparation for up-regulating expression level of low-density lipoprotein receptor in cells.

Another aspect of the invention relates to use of miRNA-96 in down-regulating the expression level of peroxisome proliferator-activated receptor-γ (PPAR-γ) in cells (e.g. in vitro or in vivo).

Another aspect of the invention relates to use of an inhibitor of miRNA-96 in up-regulating the expression level of peroxisome proliferator-activated receptor-γ (PPAR-γ) in cells (e.g. in vitro or in vivo), or in manufacturing a preparation for up-regulating the expression level of peroxisome proliferator-activated receptor-γ (PPAR-γ) in cells.

Another aspect of the invention relates to use of an inhibitor of microRNA in manufacturing a preparation or a medicament for improving the level of high density lipoprotein (HDL) in mammal and/or for reducing the level of low-density lipoprotein (LDL), cholesterol, or triglyceride in blood, wherein the microRNA is one or two or three selected from the group consisting of miRNA-96, miRNA-185, and miRNA-223.

Another aspect of the invention relates to a method for up-regulating the expression level of human scavenger receptor class B, type I, ATP-binding cassette transporter A1, low density lipoprotein-receptor, or peroxisome proliferator-activated receptor-γ in cells (e.g. in vitro or in vivo), wherein the method comprises the step of administering an inhibitor of microRNA to the cells, or the step of contacting the cells with an inhibitor of microRNA, wherein the microRNA is one or two or three selected from the group consisting of miRNA-96, miRNA-185, and miRNA-223.

Another aspect of the invention relates to a method for screening a medicament for regulating lipid metabolism or preventing or treating a disease related to lipid metabolism, comprising the step of screening an inhibitor of miRNA-96, miRNA-185 or miRNA-223; preferably comprising the steps of designing an antisense RNA of miRNA-96, miRNA-185 or miRNA-223 respectively, or contacting miRNA-96, miRNA-185 or miRNA-223 with a candidate substance respectively, detecting the expression of individual microRNA and selecting a substance specifically inhibiting expression of miRNA-96, miRNA-185 or miRNA-223.

Another aspect of the invention relates to a method for preventing or treating a disease related to lipid metabolism or for regulation of lipid metabolism, comprising the step of administering an effective amount of an inhibitor of a microRNA to a subject in need, wherein the microRNA is one or two or three selected from the group consisting of miRNA-96, miRNA-185, and miRNA-223; preferably, the disease related to lipid metabolism is, for example, hyperlipidemia caused by lipid metabolism disorders (especially hypercholesterolemia, hypertriglyceridemia and the like), atherosclerosis, cardiovascular and cerebrovascular diseases (especially coronary heart disease, myocardial infarction, stroke and the like), Alzheimer's disease, obesity, diabetes or metabolic syndrome and the like.

Another aspect of the invention relates to a method for improving the level of high density lipoprotein (HDL) in mammal and/or reducing the level of low density lipoprotein (LDL), cholesterol and triglyceride in blood, comprising the step of administering an effective amount of an inhibitor of a microRNA to a subject in need, wherein the microRNA is one or two or three selected from the group consisting of miRNA-96, miRNA-185, and miRNA-223.

As to the use, the method or the composition according to any one of aspects described above, the inhibitor of microRNA may be any substance capable of inhibiting the regulation effect of miRNA-96, miRNA-185 or miRNA-223 on a target gene, or may be a substance capable of inhibiting the expression of miRNA-96, miRNA-185 or miRNA-223, or may be a substance having specific interaction with the miRNA, for example specifically binding with the miRNA, or may be a substance capable of specifically inhibiting the interaction between the miRNA and DICER or RISC.

As to the use, the method or the composition according to any one of aspects described above, the microRNA or the inhibitor thereof can be used as a tool drug for studying the above related diseases or functional mechanisms of the above related proteins.

The present invention will be described in detail.

In the present invention, the expression "regulating lipid metabolism" or "regulation of lipid metabolism" refers to reducing the levels of cholesterol, triglyceride and/or low-density lipoprotein, and/or increasing the level of high density lipoprotein in mammals.

In the present invention, the expression "a diseases related to lipid metabolism" includes atherosclerosis, cardiovascular and cerebrovascular diseases (especially myocardial infarction, stroke), Alzheimer's disease, hyperlipidemia (especially hypercholesterolemia, hypertriglyceridemia), obesity, diabetes or metabolic syndrome.

In the present invention, the term "an inhibitor of microRNA" has the meaning well known in the art. It can be any substance capable of specific inhibiting regulation effect of miRNA-96, miRNA-185 or miRNA-223 on a target gene, or a substance specifically inhibiting expression of miRNA-96, miRNA-185 or miRNA-223 in cells, or also a substance having specific interaction with various miRNAs, for example specifically binding with various miRNAs, or may be a substance specifically inhibiting the interaction between various miRNAs and DICER or RISC.

In an embodiment of the present invention, the term "an inhibitor of a microRNA (antisense oligonucleotide inhibitor, anti-miR)" refers to a single stranded nucleic acid molecule which is synthesized and modified chemically, is complementary to specific miRNA sequence (in particular core sequence, such as position 2 to position 8 nucleotide of the sequence), or specifically inhibiting the function of endogenous miRNAs. The inhibitor of microRNA impairs the regulation effect of the endogenous miRNAs on target genes thereof and affects the expression of the target genes by specifically targeting to a single miRNA molecule (Stenvang J, Petri A, Lindow M, Obad S, Kauppinen S., Inhibition of microRNA function by antimiR oligonucleotides, Silence. 2012 Jan. 9; 3(1):1. doi: 10.1186/1758-907X-3-1). Antisense oligonucleotide inhibitors may have different lengths and chemical modifications, such as phosphorothioate modification for phosphate backbone, 2'-O-alkylation modification for ribose including 2'-O-methyl, 2'-O-methoxyethyl, 2'-F, and so on, as well as peptide nucleic acid (PNA) modification, locked nucleic acid (LNA) modification, and so on.

In context of the uses described above, the microRNA or the inhibitors thereof may be used alone or may be linked to other molecules, such as cholesterol, target cellular receptor and the like, or may be cloned into a vector.

In the present invention, the term "cell" refers to the cell containing an binding site of miR-96, miR-185 or miR-223, or regulated by miR-96, miR-185, miR-223 or the inhibitor thereof, in particular to a cell in which SR-BI protein, or other proteins related to cholesterol or lipid metabolism can be regulated by miR-96, miR-185, miR-223 or the inhibitor thereof. In an embodiment of the present invention, the cell includes liver cell (for example, hepatocyte), monocyte-macrophage, and cell in tissue of liver, kidney, heart, intestine, lung and spleen.

In this invention, the expression "up-regulating or down-regulating the expression level of a certain protein in the cell" refers to up-regulating or down-regulating the level of mRNA or protein of said proteins in the cell; wherein the up-regulating or down-regulating is determined by comparing with the cell without treatment.

In an embodiment of the present invention, by combination of real-time quantitative PCR and flow cytometry, it is confirmed that miR-96, miR-185 and miR-223 can significantly down-regulate the expression level of mRNA and protein of SR-BI gene in hepatocytes, while their antisense oligonucleotide inhibitors have the opposite function. In the analysis for Dil-HDL uptake in the cell with flow cytometry, it is found that miR-96, miR-185 and miR-223 can remarkably inhibit Dil-HDL uptake in the hepatocyte, while their corresponding antisense oligonucleotide inhibitors have the opposite function. The inhibition effect of miR-185 on Dil-HDL uptake in the hepatocyte is abolished after SR-BI gene is silenced, which proves that SR-BI, the key molecule in the process of reverse cholesterol transport, is effectively regulated by miR-96, miR-185 and miR-223.

In a embodiment of the present invention, in order to determine the binding sites of these miRNAs, PCR is used to amplify the fragments of 3' untranslation region (3'UTR) of SR-BI gene with different lengths as well as the fragments of 3' untranslation region (3'UTR) of SR-BI gene with corresponding binding sites of these miRNAs deleted, and then these fragments are constructed to the downstream of luciferase reporter gene and transfected into HepG2 cells. By using luciferase assays, it is found that miR-96, miR-185 and miR-223 are capable of significantly inhibiting the expression of luciferase reporter gene. Moreover, the binding sites of these miRNAs are determined by nucleotide deletion, which shows that the binding sites of miR-96, miR-185, and miR-223 are located in different regions of 3'UTR of SR-BI gene. The results of experiments involving combined miR-96, miR-185 and miR-223 show that these miRNAs regulate posttranscriptional expression of SR-BI gene in a synergic manner.

In an embodiment of the present invention, the distributions of miR-96 and miR-185 are tested in different tissues in mice. The results of quantitative analysis for miRNAs show that miR-96 and miR-185 are distributed in liver of mice with certain levels. The expressions of miR-96 and miR-185 are further determined in liver of ApoE-knockout mice fed on high fat diet. The results show that the total cholesterol levels and LDL cholesterol levels in serum are significantly increased, and the mice exhibit the hyperlipidemia characteristics, and the expression of SR-BI was significantly increased in liver, and the expression levels of miR-96 and miR-185 are significantly decreased, in comparison to the mice fed on a normal diet. This negative correlation further confirms the regulation of these miRNAs on SR-BI.

Considering the key role of macrophages in the SR-BI mediated reverse cholesterol transport process, in an embodiment of the present invention, the distributions and functions of miR-96, miR-185 and miR-223 are determined in human monocyte macrophages THP-1 induced by phorbol ester (PMA). From the results, it is shown that miR-185 and miR-96 may significantly reduce the mRNA level of SR-BI in macrophages (THP-1 induced by PMA) and miR-223 does not have the effect.

In an embodiment of the present invention, the regulation effects of miR-96, miR-185 and miR-223, especially miR-185 and miR-96 on other related and predicted target genes are detected. In the study with ABCA1 which is the key molecule of the first speed limiting component in RCT, it is shown that there are one binding site for miR-96 and one binding site for miR-223 in the 3'UTR of ABCA1 gene. The alignment result of the sequences from multi-species confirms that the binding sites are highly conserved. The analysis using small RNA transfection and real-time RT-PCR shows that miR-96 and miR-223 can significantly down-regulate the mRNA level of ABCA1 in hepatocytes, and their antisense oligonucleotide inhibitors can significantly up-regulate the mRNA level of ABCA1, which confirms that miR-96 and miR-223 can effectively regulate ABCA1.

In an embodiment of the present invention, in the study with LDLR, it is shown that there are two binding sites of miR-185 in 3'UTR of LDLR, and the alignment results of the sequence from multi-species demonstrate that these sites are very conserved. The analysis using small RNA transfection and real-time RT-PCR shows that miR-185 can significantly down-regulate the mRNA level of LDLR in hepatocytes, and their antisense oligonucleotide inhibitors can significantly up-regulate the mRNA level of LDLR, which confirms that miR-185 can effectively regulate LDLR.

In an embodiment of the present invention, in the studies on PPAR-γ, which is an important transcription factor regulating the balance between cholesterol and lipid metabolism, it is shown that there is one binding site of miR-96 in its 3° UTR, and the alignment results of the sequence from multi-species confirm that the binding site is highly conserved. The analysis using small RNA transfection and real-time RT-PCR shows that miR-96 can significantly down-regulate the mRNA level of PPAR-γ in hepatocytes, and its antisense oligonucleotide inhibitor can significantly up-regulate the mRNA level of PPAR-γ, which confirms that MiR-96 can effectively regulate PPAR-γ.

Advantages of the Invention

The invention determines a series of important targets in process of lipid metabolism regulated by miR-96, miR-185, miR-223. These targets play important roles in regulation of lipid metabolism. MiR-96, miR-185 and miR-223 can be used as medical compositions or biological markers, or can be used as targets for novel drug discovery and their inhibitors can be used as medical compositions, for preventing or treating the related diseases caused by lipid metabolism disorder such as hyperlipidemia, atherosclerosis and coronary heart disease.

BRIEF DESCRIPTION OF THE DRAWINGS

FIG. 1 shows the effects of gene silencing of Dicer or Drosha on SR-BI mRNA level; wherein the left shows the mRNA level of SR-BI after Dicer or Drosha is silenced; the middle shows the mRNA level of Drosha after Drosha is silenced; the right shows the mRNA level of Dicer after Dicer is silenced; Scr-si represents the control sequence of siRNA (Invitrogen, 12935-200, 12935-300, 12935-400), Drosha-si (invitrogen, HSS120887) represents the group of Drosha gene silencing, and Dicer-si (invitrogen, HSS118719) represents the group of Dicer gene silencing. *$P<0.05$, **$P<0.01$, in comparison to scr-si.

FIG. 2 shows the predicted targets of mirR-96, miR-185 and miR223 in 3'UTR of SR-BI.

FIG. 3 shows sequence conservation in multiple species of predicted targets of mirR-96, miR-185 and miR223 in 3'UTR of SR-BI (Hsa, human; Ptr, chimpanzees; Mml, Macaque; Ssc, pig; Bta cattle; Eca, horse; Cfa, dog; Fca, cat; Mmu, mouse; Cpo, Guinea pig; Rno, rattus norvegicus; OCU, rabbits; Ete, Hedgehog).

FIG. 9 shows the sequence conservation in multiple species of predicted targets of mirR-96 and miR223 in 3'UTR of ABCA1 (Hsa, human; Pt, chimpanzees; Pab, Sumatra chimpanzees; Ame, giant panda; Mmu, mouse).

FIG. 10 shows regulation effects of miR-96, miR-223 and their antagonists on the mRNA level of ABCA1; wherein anti-miR represents miRNA antagonists, and ctl-miR represents miRNA control. **P<0.01, in comparison to ctl-miR (miR); ##P<0.01, in comparison to ctl-miR (anti-miR).

FIG. 11 shows the two targets of miR-185 in 3'UTR of LDLR.

FIG. 12 shows the sequence conservation in multiple species of predicted targets of miR-185 in 3'UTR of LDLR (Hsa, human; Ptr, chimpanzees; pab, Sumatra chimpanzees; Bta cattle).

FIG. 13 shows regulation effects of miR-185 and its antagonist on the mRNA level of LDLR; wherein anti-miR represents miRNA antagonist, and ctl-miR represents miRNA control. **P<0.01, in comparison to ctl-miR (miR); # P<0.05, in comparison to ctl-miR (anti-miR).

FIG. 14 shows one predicted target of miR-96 in 3'UTR of PPAR-γ.

FIG. 15 shows sequence conservation of predicted target of miR-96 in 3'UTR of PPAR-γ in multiple species (Hsa, human; Ptr, chimpanzees; pab, Sumatra chimpanzees; Ssc, pig; Bta cattle; Fca, cat; Mmu, mouse; Rno, *rattus norvegicus*; Gga, chicken).

FIG. 19 shows regulation of HDL on the mRNA level of miR-185 and SR-BI, wherein Veh represents the solvent control. *P<0.05, **P<0.01, in comparison to veh (mir-185); #P<0.05, in comparison to veh (SR-BI).

FIG. 20 shows distribution of miR-96, miR-185, or miR-223 in different tissues or cells in ApoE-knockout mice; wherein A represents abundances of miR-96 or miR-185 in different tissues (liver, kidney, heart, intestines, lungs, and spleen); B represents abundances of miR-96, miR-185 or miR-223 in different cells (human liver cancer cell line HepG2 and Bel-7402, normal liver parenchyma cells HL-7702 and THP-1 macrophages induced with PMA for 24 hours).

SPECIFIC MODELS FOR CARRYING OUT THE INVENTION

Figure 4:
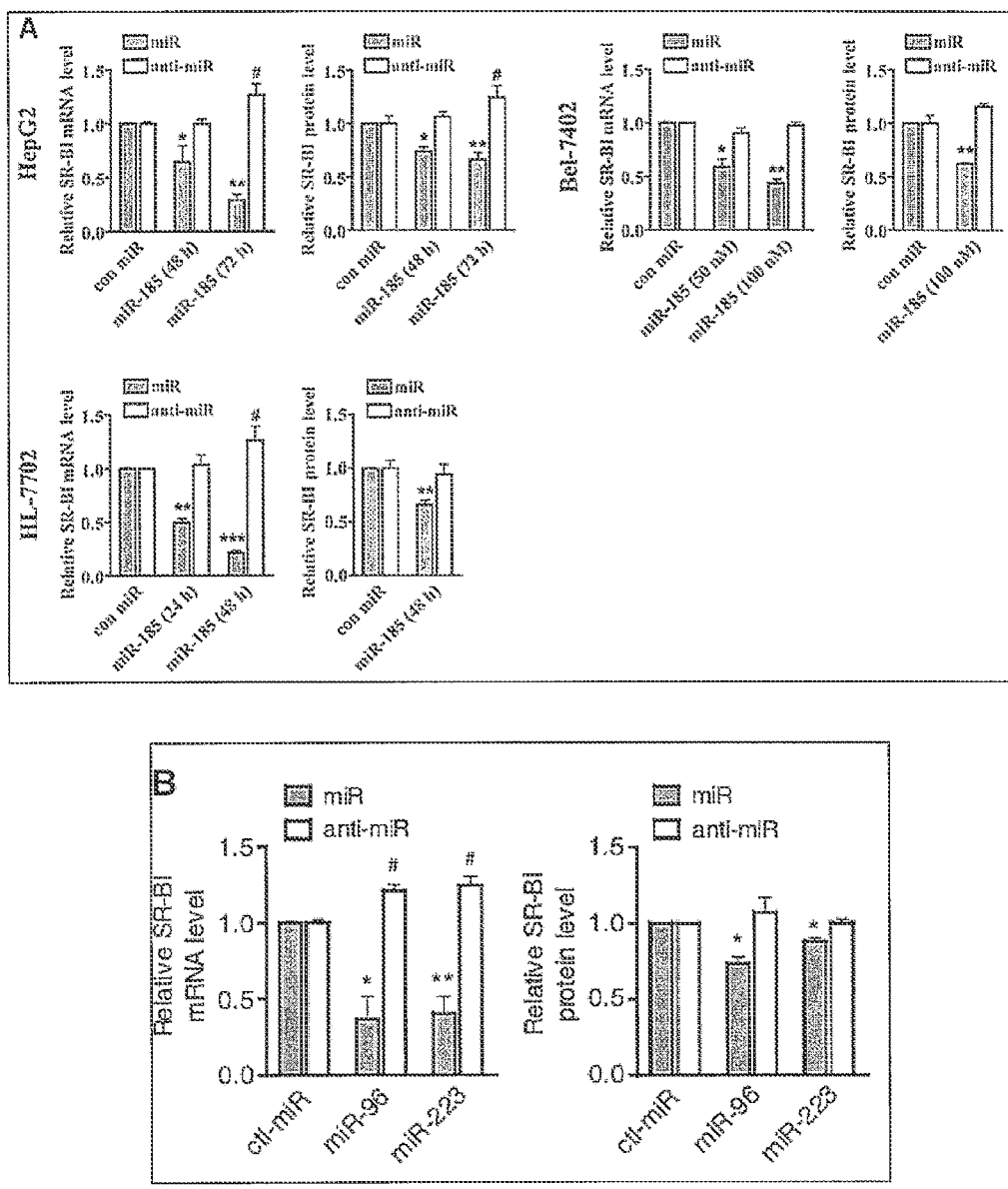
FIG. 4 shows regulatory effects of miR-96, miR-185, miR-223 and its antagonist on the mRNA level and protein expression level of SR-BI, wherein A represents the mRNA and protein level of SR-BI determined at different time after miR-185 and antisense oligodeoxynucleotide inhibitor thereof are transiently transfected into human hepatoma HepG2 and Bel-7402 or human normal hepatocyte HL-7702 using lipofectamine RNAiMAX transfection reagent; B represents changes in the mRNA and protein level of SR-BI after miR-96, miR-223 or their antisense oligonucleotide inhibitors are transiently transfected into hepatoma HepG2 using lipofectamine RNAiMAX transfection reagent. *$P<0.05$, $P<0.01$, *$P<0.001$, in comparison to ctl-miR (miR); #$P<0.05$, in comparison to ctl-miR (anti-miR). (con miR in Figure A and ctl-miR in Figure B are the same)

The embodiments of the invention are illustrated in detail by referring to the examples, but those skilled in the art would understand that the following examples are merely for illustrating the invention and should not be deemed as restriction of the invention. The examples in which specific conditions are not indicated are performed according to conventional conditions or conditions suggested by manufacturers. The reagents or instruments for which manufacturers are not indicated are all conventional products commercially available.

Materials and Methods
1. Material
1.1 The plasmids, cell lines and animals: eukaryotic cell expression vector pcDNA3.1 and pGL3-Basic are products from Promega in United States. The human hepatoma cell line HepG2, Bel-7402 and HL-7702 are kept in our laboratory (HepG2 is purchased from ATCC, HB-8065, Bel-7402 and HL-7702 are purchased from institute of Basic Medical Sciences, Chinese Academy of Medical Sciences) and the ApoE-knockout mice are purchased from Peking University Health Science Center.

1.2 Primary Reagent: A cell lysate for DNA extraction and a luciferase assay system and a RNA extraction Kit (SV Total RNA Isolation System) are purchased from Promega in United States. A transfection reagent (Lipofectamine™ 2000) and a reverse transcription Kit (SuperScript III First-Strand) are purchased from Invitrogen in United States. A real-time fluorescent quantitative PCR kit (FastStart Universal SYBR Green PCR Master) is purchased from Roche. A RNA extraction Mini Kit (miRNeasy Mini Kit), A small RNA RT Kit (miScript II RT Kit) and a fluoresence Quantitative assay Kit (miScript SYBR Green PCR Kit) are purchased from Qiagen in United States. cell culture medium MEM is purchased from Thermo in United States. Fetal bovine serum, sodium pyruvate, non-essential amino acid and antibiotic G418 are purchased from Gibco in United States. Dimethyl sulfoxide (DMSO) is purchased from Sigma in United States.

1.3 Apparatus: MiniCycle PTC-200 PCR is the product from MJ Research in United States; EnVision multi-functional microplate detector is the product from PerkinElmer in United States; and Real-time fluorescence quantitative PCR instrument-iQ5 Multicolor Real-Time PCR is the product from Bio-Rad.

2 Methods 2.1 Construction of recombinant plasmid pc-luc-3'UTR: 3'UTR sequence of CLA-1 (NM_005505) is obtained by PCR and is cloned into downstream of luciferase reporter gene of plasmid pc-luc (inserting luciferase reporter gene into multiple cloning site of plasmid vector pcDNA3.1 to construct plasmid pc-luc) to obtain the recombinant plasmid pc-luc-3'UTR, which are confirmed by sequencing.

2.2 Cell culture and transfection: HepG2 cells and the like are cultured at 37, in 5% $CO_2$ in MEM medium containing 10% fetal bovine serum, 1 mmol/L sodium pyruvate and 1% non-essential amino acids. The plasmids used for transfection are extracted according to instructions of PureYield™ Plasmid Midiprep System kit. $1 \times 10^5$ HepG2 cells are seeded on 30 mm Petri dishes. When the cells grow adhering to the wall and the convergence degree is about 80%, pc-luc-3'UTR or miRNA is transiently transfected into HepG2 cells using liposome Lipofectamine™ 2000 or Lipofectamine RNAiMAX. The detection is carried out a certain time post transfection.

2.3 Real-Time fluorescent quantitative PCR: Total RNA is extracted from cells, cDNA is synthesized using a kit of SuperScript III First-Strand (Invitrogen) or miScript II RT Kit, the fluorescence quantitative PCR reaction is performed using 2×TaqMan® Gene Expression Master Mix or miScript SYBR Green PCR Kit, and the analysis is performed with data analysis software and the Ct value is calculated. GAPDH or U6 is used as an internal control, and the transcription level of luciferase gene is quantified using the relatively Ct method.

2.4 Detection of expression levels of the proteins on cell surface: cells are seeded at density of $1 \times 10^5$/ml on 24-well cell culture plates, digested and collected after treatment, fixed with 4% paraformaldehyde for 4 h, and are resuspended in 1 ml PBS containing 5% FBS and left to stand for 15 min at 4° C. The primary antibody (1:500) and the FITC-labeled secondary antibody (1:1000) are added respectively and each is incubated for 50 min. After rinsed with PBS, filtration is carried out through the 300 mesh of nylon membrane and the detection is performed using flow cytometry. The average number of cells detected in each of sample groups is 10,000. The relative fluorescence intensity of cells in each group is shown as the figure of logarithmic integral.

2.5 Determination of cellular function for Dil-HDL uptake: Effect of compound on cellular Dil-HDL uptake is determined using flow cytometry. After HepG2 cells and the like are passaged, the cells are seeded at density of $1 \times 10^5$ cells/ml on 24-well cell culture plate. After treatment, 2 µg/ml of Dil-HDL is added and incubation is carried out at 37° C. for 4 h. The cells are digested and collected, resuspended in 700 µl PBS and filtered through 300 mesh of nylon membrane. The cellular fluorescence is determined using flow cytometry. The average 10,000 cells are determined for each sample. The relative fluorescence intensity of cell in each group is shown as the figure of logarithmic integral.

Process for Screening miRNA

Predicted miRNAs are transfected into HepG2 cells to determine effects of miRNA on the expression of SR-BI using real-time quantitative PCR.

The selected miRNAs are miR-96, miR-185 and miR-223, of which sequences are as follows:

```
hsa-miR-96
                                (SEQ ID NO: 1)
5'-uuuggcacuagcacauuuuugcu-3' hsa-miR-185
                                (SEQ ID NO: 2)
5'-uggagagaaaggcaguuccuga-3' hsa-miR-223
                                (SEQ ID NO: 3)
5'-ugucaguuugucaaauacccca-3'
```

These miRNAs of the present invention are commercially available from QIAGEN, wherein hsa-miR-96 with Cat. No. MSY0000095, hsa-miR-185 with Cat. No. MSY0000455, and hsa-miR-223 with Cat. No. MSY0004570.

Example 1

Regulatory Effects of miR-96, miR-185 and miR-223 on SR-BI which is an Important Target in Reverse Cholesterol Transport 1.1, Effects of Dicer and Drosha Gene Silencing on the mRNA Level of SR-BI Two key enzyme, Dicer and Drosha, in microRNA biosynthesis are knocked out by siRNA gene silencing, and then the mRNA level of SR-BI is detected by Real-time RT-PCR.

From experimental results, it is shown that the mRNA level of SR-BI is up-regulated significantly after Dicer and Drosha genes are silenced, indicating microRNAs are involved in regulation of SR-BI (as shown in FIG. 1).

1.2, Regulatory Effects of miR-96, miR-185, miR-223 and their Antagonists Thereof on the mRNA and Protein Expression Level of SR-BI.

The miRNA antagonists (anti-miR) in the present invention are purchased from QIAGEN, and their sequences and catalogue numbers are as follows:

```
anti-miR-96 (Cat. No. MIN0000095)
                                (SEQ ID NO: 4)
5'-agcaaaaaugugcuagugccaaa-3' anti-miR-185 (Cat. No. MIN0000455)
                                (SEQ ID NO: 5)
5'-ucaggaacugccuuucucucca-3'
```

-continued anti-miR-223 (Cat. No. MIN0004570)
(SEQ ID NO: 6)
5'-uggggguauuugacaaacugaca-3'

The control of miRNA antagonists is available from QIAGEN, with Cat. No. 1027271.

With lipofectamine RNAi MAX transfection reagent, miR-96, miR-185, miR-223 and antisense oligonucleotide inhibitors thereof are transiently transfected into human hepatoma cells HepG2 or Bel-7402 and human normal heptical cell HL-7702. The total cellular RNA is extracted using RNA extraction Mini Kit (Promega) 48 or 72 hours after transfection, and the reverse transcript is performed using cDNA synthesis Kit (Invitrogen), and SR-BI mRNA level is determined by Real-time RT-PCR. With lipofectamine RNAi MAX transfection reagent, miR-96, miR-185, miR-223 and antisense oligonucleotide inhibitors thereof are transiently transfected into hepatocarcinoma cells HepG2 or Bel-7402 and normal heptical cell HL-7702. The change in expression level of SR-BI protein is determined by flow cytometry 48 or 72 hours after transfection.

Figure 5:
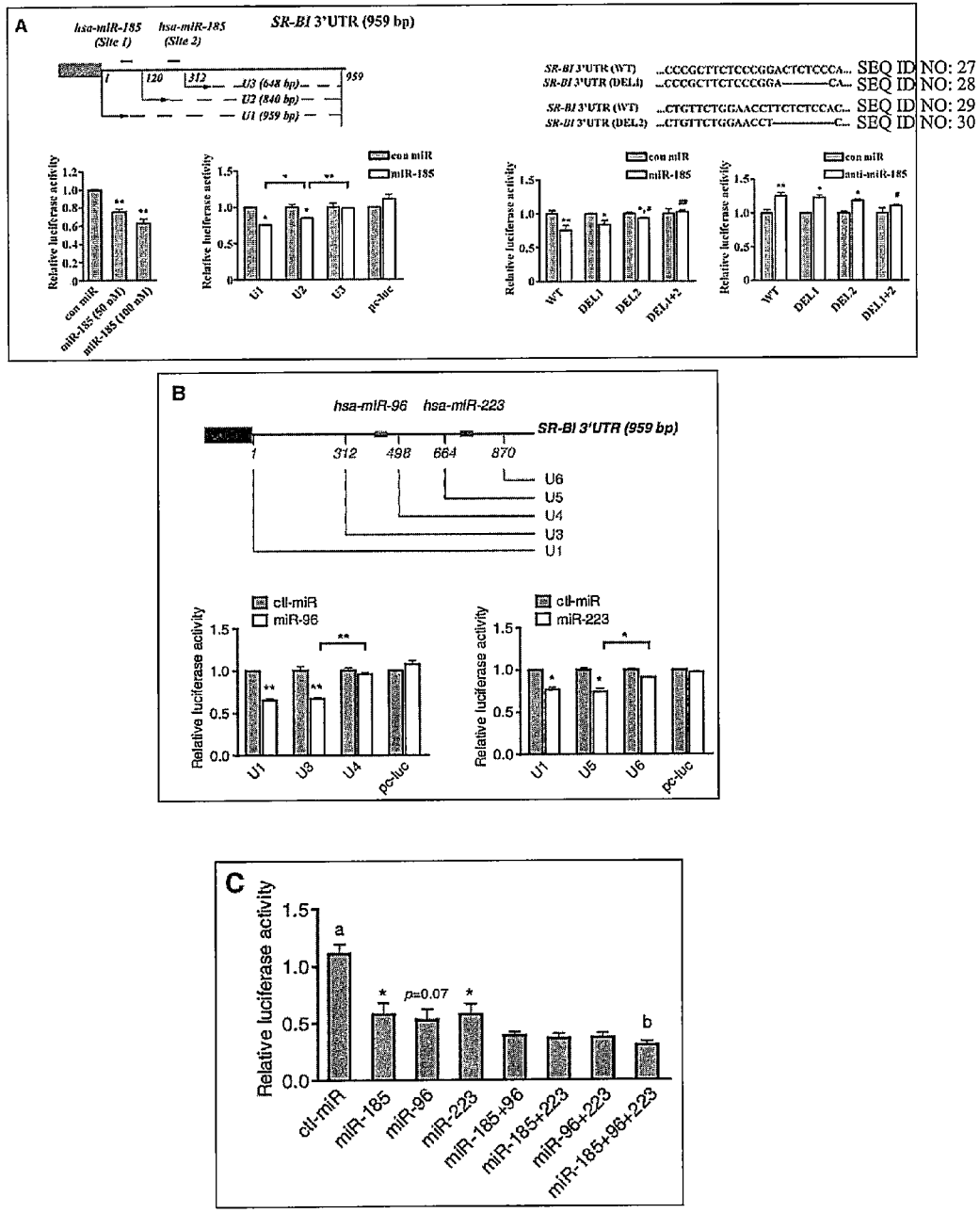
FIG. 5 shows verification of direct binding sites of miR-96, miR-185 and miR-223 in 3'UTR of SR-BI; wherein A shows that miR-185 can significantly reduce the expression of luciferase reporter gene in the presence of corresponding predicted target of miR-185 in 3'UTR fragment of SR-BI, while miR-185 cannot significantly reduce the expression of luciferase reporter gene in the absence of corresponding predicted target in 3'UTR fragment of SR-BI; B shows that miR-96 and miR-223 can significantly reduce the expression of luciferase reporter gene in the presence of corresponding predicted targets of miR-96 and miR-223 in 3'UTR fragment of SR-BI; C shows the effects of miR-96, miR-185 and miR-223 alone or in combination on the expression of luciferase reporter gene, which confirms that miR-96, miR-185 and miR-223 have synergetic effects; wherein anti-miR represents miRNA antagonists (antisense oligonucleotide inhibitors), ctl-miR represents miRNA control (5'-UG-GAAUGUAAAGAAGUAUGUAU-3', SEQ ID NO: 7), pc-luc represents a control plasmid with no 3'UTR of SR-BI; the nucleotide sequence of U1 is full-length of 3'UTR fragment of SR-BI (959 bp), the nucleotide sequence of U2 is the $120^{th}$-$959^{th}$ bp of 3'UTR fragment of SR-BI, the nucleotide sequence of U3 is the $312^{th}$-$959^{th}$ bp of 3'UTR fragment of SR-BI; the nucleotide sequence of U4 is the $498^{th}$-$959^{th}$ hp of 3'UTR fragment of SR-BI; the nucleotide sequence of U5 is the $664^{th}$-$959^{th}$ bp of 3'UTR fragment of SR-BI, the nucleotide sequence of U6 is the $870^{th}$-$959^{th}$ bp of 3'UTR fragment of SR-BI, WT represents wild type of 3° UTR fragment of SR-BI, DEL1 represents 3'UTR fragment of SR-BI lacking binding site 1 for miR-185, and DEL2 represents 3'UTR fragment of SR-BI lacking binding site 2 for miR-185. *P<0.05, **P<0.01, in comparison to ctl-miR; #P<0.05, ## P<0.01, in comparison to the wild-type vector.

From experimental results, it is shown that expression levels of mRNA and protein of SR-BI are down-regulated by miR-96, miR-185 and miR-223 in hepatocyte (as shown in FIG. 5).

1.3, Prediction of miRNA Targeting 3'UTR of SR-BI Gene and Homology Analysis of Target Sites It is predicted that miRNAs such as miR-96, miR-185 and miR-223 directly bind on 3'UTR of SR-BI (NM_005505) using MicroRNA.org (www.microrna.org) and TargetScan (www.targetscan.org) and other online software. Using software Clustal X2, 3'UTR of SR-BI of multiple species are aligned.

The predicted results are shown in FIG. 2. There are one predicted target of miR-96 and one predicted target of miR-223 in 3'UTR of SR-BI and there are two predicted targets of miR-185 in 3'UTR of SR-BI. The results of sequence alignment are shown in FIG. 3. The sequence of the predicted targets of miR-96, miR-185 and miR-223 in 3'UTR of SR-BI are conserved in multiple species (Hsa, human; Ptr, chimpanzees; Mml, Macaque; Ssc, pig; Bta, cattle; Eca, horse; Cfa, dog; Fca, cat; Mmu, mouse; Cpo, Guinea pig; Rno, *rattus norvegicus*; Ocu, rabbit; Ete, Hedgehog).

1.4, Verification of Direct Binding Sites of miR-96, miR-185 and miR-223 in 3'UTR of SR-BI The luciferase reporter gene is inserted into multiple cloning site of the plasmid vector pcDNA3.1 to construct the plasmid pc-luc. According to the predicted targets of miR-96, miR-185 and miR-223, different length of 3'UTR fragments of SR-BI are amplified by PCR method, or prediction targets of miR-185 are removed from 3'UTR of SR-BI using overlap PCR method to obtain a series of different length 3'UTR fragments of SR-BI. The different length of 3'UTR fragments of SR-BI are inserted into downstream of luciferase reporter gene of plasmid vector pc-luc. By transient transfection method and using Lipofectamine RNAiMAX transfection reagent, the constructed plasmid pc-luc containing a series of different length of 3'UTR fragments of SR-BI, miR-96, and miR-185, miR-223 or their antisense oligonucleotides acid inhibitors are transfected into HepG2 cells, and after 48 hours, the expression activities of the luciferase reporter genes are determined by luciferase reporter gene analysis.

The results shown in FIG. 4 show that if there are corresponding predicted targets of miR-96, miR-185 and miR-223 in the 3'UTR fragment of SR-BI, miR-96, miR-185 and miR-223 can significantly reduced the expression activities of luciferase reporter genes; if there are not, miR-96, miR-185 and miR-223 cannot significantly reduced the expression activities of luciferase reporter genes. Experimental results verify the targets of miR-96, miR-185 and miR-223 in 3'UTR of SR-BI, and further experiments confirm that there are synergistic effects between these miRNAs.

1.5, Effects of miR-96, miR-185 and miR-223 on Dil-HDL (Dil Fluorescein-Labeled HDL) Uptake in Hepatocytes.

miR-96, miR-185, miR-223, or antisense oligonucleotide inhibitors thereof are transiently transfected into hepatocarcinoma cells HepG2, Bel-7402, and normal hepatocytes HL-7702 by Lipofectamine RNAiMAX reagent (Invitrogen), and after 72 hours, the cells are incubated with 2 μg/mL Dil-HDL for 4 hours. Then Dil-HDL uptake by hepatocytes is determined by flow cytometric.

Figure 6:
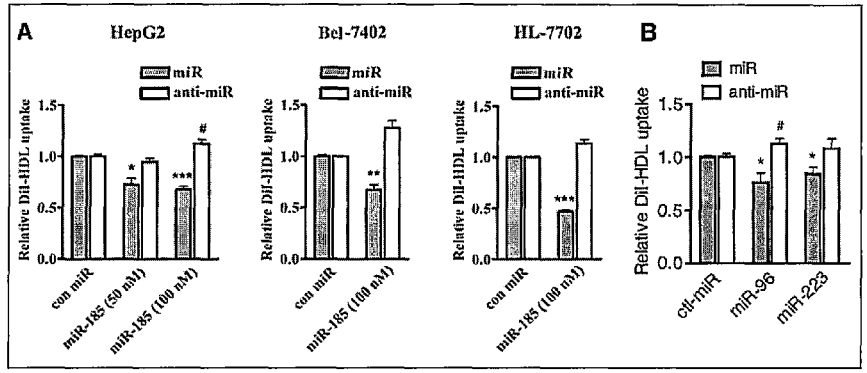
FIG. 6 shows the effect of miR-96, miR-185 and miR-223 on Dil-HDL uptake in hepatocytes; A: detecting Dil-HDL uptake in hepatocytes by flow cytometry, wherein the hepatocytes are obtained by the following steps: transiently transfecting hepatoma HepG2 and Bel-7402 or normal hepatocyte HL-7702 with miR-185 or antisense oligonucleotide inhibitor thereof using lipofectamine RNAiMAX transfection reagent, and after 72 hours, incubating the cells with 2 µg/mL Dil-HDL for 4 hours; B: detecting Dil-HDL uptake in hepatocytes by flow cytometry, wherein the hepatocytes are obtained by the following steps: transiently transfecting hepatoma HepG2 with miR-96, miR-223 or antisense oligonucleotide inhibitors thereof using lipofectamine RNAiMAX transfection reagent, and after 72 hours, incubating the cells with 2 µg/mL Dil-HDL for 4 hours; CU-miR represents control miRNA, anti-miR represents miRNA antagonist; *P<0.05, P<0.01, *P<0.001, in comparison to ctl-miR (miR); #P<0.05, in comparison to ctl-miR (anti-miR).

The results show that Dil-HDL uptake decreases significantly in hepatocytes after transfected with miR-96, miR-185, miR-223, and Dil-HDL uptake increases significantly in three kinds of hepatocytes after transfected with antisense oligonucleotide inhibitors of miR-96, miR-185 and miR-223, which shows that miR-96, miR-185, miR-223 can inhibit HDL uptake in hepatocytes, and the antisense oligonucleotide inhibitors of miR-96, miR-185, miR-223 can increase HDL uptake in hepatocyte (as shown in FIG. 6).

1.6, Effect of SR-BI Gene on Inhibition of Dil-HDL Uptake in Hepatocyte Mediated by miR-185

After SR-BI gene is knocked out using siRNA gene silencing, the expression of SR-BI protein is significantly reduced in HepG2 cells. After transient transfection of miR-185 for 72 hours, the cells are incubated with 2 μg/mL Dil-HDL for 4 hours. Then the Dil-HDL uptake is determined by flow cytometry in hepatocyte.

Figure 7:
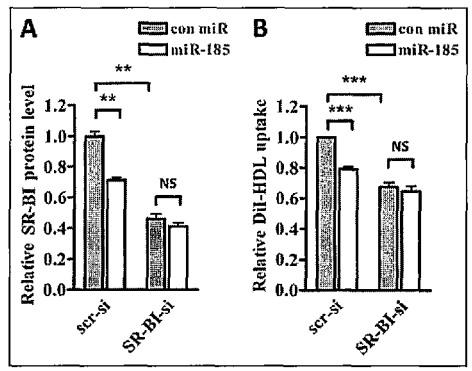
FIG. 7 shows effects of SR-BI on inhibition of Dil-HDL uptake mediated by miR-185 in hepatocyte; wherein ctl-miR represents control miRNA, scr-si represents siRNA control, and SR-BI-si represents the group of SR-BI gene silencing. P<0.01; *P<0.001; NS, no significant differences.

The results shown in FIG. 7 show that the effect of down-regulating Dil-HDL uptake by miR-185 disappears after SR-BI gene is silenced, which proves that miR-185 inhibits Dil-HDL uptake in hepatocyte through SR-BI gene.

Example 2

Regulatory Effects of miR-96 and miR-223 on ABCA1, an Important Target of Reverse Cholesterol Transport 2.1, Prediction of Targets of miR-96 and miR-223 in 3'UTR of ABCA1 and Homology Analysis The binding sites of miR-96 and miR-223 in 3'UTR of ABCA1 are predicted using MicroRNA.org and TargetScan. Sequences of predicted targets of miR-96 and miR-223 in 3'UTR of ABCA1 are aligned in multiple species using Clustal X2 software.

Figure 8:
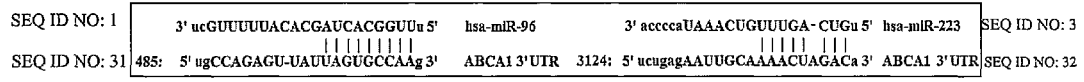
FIG. 8 shows predicted targets of miR-96 and miR-223 in 3'UTR of ABCA1.

The predicted results are shown in FIG. 8. There are one target of miR-96 and one target of miR-223 in 3'UTR of ABCA1. The results of sequence alignment are shown in FIG. 9. The sequence of the predicted targets of miR-96 and miR-223 in 3'UTR of ABCA1 are conserved in multiple species (Has, human; Ptr, chimpanzee: Pab, Sumatra chimpanzees; Ame, giant panda; Mmu, mouse).

2.2, Regulatory Effects of miR-96, miR-223 and their Antagonist on the mRNA Level of ABCA1

Hepatoma cells HepG2 are transiently transfected with miR-96, miR-223 or their antisense oligonucleotide inhibitors using Lipofectamine RNAiMAX Transfection reagent (Invitrogen), and after 72 hours, the total RNA is extracted using RNA extraction mini kit (Promega) and is reverse transcribed using cDNA synthesis Kit (Invitrogen), and mRNA level is determined by real-time RT-PCR assay.

The results are shown in FIG. 10. MiR-96 and miR-223 can significantly reduce mRNA levels of ABCA1 in HepG2 cells, and their antisense oligonucleotide inhibitors can significantly increase the mRNA levels of ABCA1 in HepG2 cells.

Example 3

Regulatory Effects of miR-185 and its Antagonists on LDLR 3.1, Prediction of Targets of miR-185 in 3'UTR of LDLR and Homology Analysis The binding sites of miR-185 in 3'UTR of LDLR are predicted using MicroRNA.org and TargetScan. Sequences of predicted targets of miR-185 in 3'UTR of LDLR are aligned in multiple species using Clustal X2 software.

The predicted results are as shown in FIG. 11. There are two predicted targets of miR-185 in 3'UTR of LDLR. The results of sequence alignment are shown in FIG. 12. The sequence of the predicted targets of miR-185 in 3'UTR of LDLR are conserved in multiple species (Has, human; Ptr, chimpanzee; Pab, Sumatra chimpanzees; Bta, cattle).

3.2, Regulation Effects of miR-185 and its Antagonist on the mRNA Level of LDLR

Hepatoma cells HepG2 are transiently transfected with miR-185 or its antisense oligonucleotide inhibitors using Lipofectamine RNAiMAX Transfection reagent (Invitrogen), and after 72 hours, the total RNA is extracted using RNA extraction mini kit (Promega) and is reverse transcribed using cDNA synthesis Kit (Invitrogen), and mRNA level is determined by real-time RT-PCR assay.

The results are shown in FIG. 13. MiR-185 can significantly reduce LDLR mRNA levels in cells HepG2, and their antisense oligonucleotide inhibitors can significantly increase the mRNA level of LDLR in cells HepG2.

Example 4

Regulation Effects of miR-96 and its Antagonists on PPAR-γ

4.1, Prediction of Targets of miR-96 in 3'UTR of PPAR-γ and Homology Analysis

The binding sites of miR-96 in 3'UTR of PPAR-γ are predicted using MicroRNA.org and TargetScan. Sequences of predicted targets of miR-96 in 3'UTR of PPAR-γ are aligned in multiple species using Clustal X2 software.

The predicted results are as shown in FIG. 14. There is one target of miR-96 in 3'UTR of PPAR-γ. The results of sequence alignment are shown in FIG. 15. The sequence of the predicted targets of miR-96 in 3'UTR of PPAR-γ are conserved in multiple species (Has, human; Ptr, chimpanzee; Pab, Sumatra chimpanzees; Ssc, pig; Bta, cattle; Fca, cat; Mmu, mouse; Rno, *Rattus norvegicus*; Gga, chicken).

4.2, Regulatory Effects of miR-96 and its Antagonist on the mRNA Level of PPAR-γ

Hepatoma cells HepG2 are transiently transfected with miR-96 or its antisense oligonucleotide inhibitor using Lipofectamine RNAiMAX Transfection reagent (Invitrogen), and after 72 hours, the total RNA is extracted using RNA extraction mini kit (Promega) and is reverse transcribed using cDNA synthesis Kit (Invitrogen), and mRNA level is determined by real-time RT-PCR assay.

Figure 16:
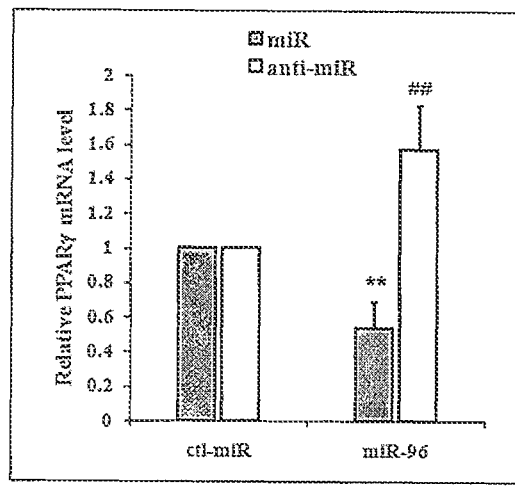
FIG. 16 shows regulatory effects of miR-96 and its antagonist on the mRNA level of PPAR-γ; wherein anti-miR represents miRNA antagonist, and ctl-miR represents miRNA control. **P<0.01, in comparison to ctl-miR (miR); ## P<0.01, in comparison to ctl-miR (anti-miR).

The results are shown in FIG. 16, miR-96 can significantly reduce the mRNA level of PPAR-γ in HepG2 cells, and its antisense oligonucleotide inhibitors can significantly increase the mRNA level of PPAR-γ in HepG2 cells.

Example 5

Effects of miR-96, miR-185 and miR-223 on Regulation of Lipid Metabolism 5.1, Regulatory Effects of HDL on mRNA Levels of miR-185 and SR-BI.

After hepatoma cells HepG2 are incubated with HDL, the abundance of miR-185 and the mRNA level of SR-BI are determined by Real-time RT-PCR assay.

Experimental results show that the abundance of miR-185 is significantly down-regulated in a dosage-dependent manner, and the mRNA levels of SR-BI are significantly up-regulated in a dosage-dependent manner (FIG. 19), which suggests that miR-185 and SR-BI are both involved in lipid regulation mediated by HDL.

5.2, Distributions of miR-96, miR-185 or miR-223 in Different Tissues of ApoE-Knockout Mice or Cell Lines.

Tissues from liver, kidney, heart, intestine, lung, spleen and other organs from ApoE-knockout mice, and cell lines such as human hepatoma cell HepG2 and Bel-7402, normal hepatocyte HL-7702 and macrophage THP-1 induced by PMA for 24 hours are taken as the samples, and the abundances of miR-96, miR-185 and miR-223 in different tissues or cells are determined by real-time RT-PCR assay.

The results show that miR-185 and miR-96 present high expression in the tissues from liver, kidney, heart and other organs from mice, and human hepatocytes and macrophages. MiR-223 presents high expression in human macrophages (FIG. 20).

5.3, Expression Levels of miR-96 and miR-185 in Liver in High Fat Diet Fed Mice.

ApoE knockout mice are fed on high-fat diet for 8 weeks, blood was taken from orbit and the total cholesterol level and LDL cholesterol level in serum are determined. Meanwhile, the liver is taken as sample, and the abundances of miR-96 and miR-185 are determined by real-time RT-PCR assay (Qiagen).

Figure 17:
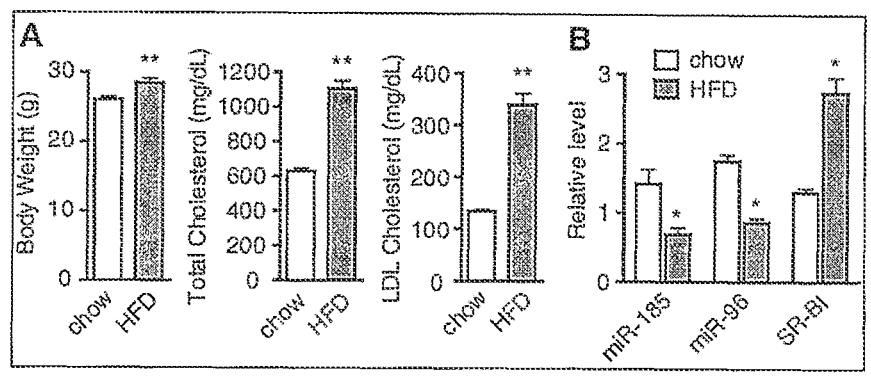
FIG. 17 shows expression levels of miR-96 and miR-185 in liver in high fat diet fed mice, wherein the first picture shows body weight of mice, the second picture shows total cholesterol level, the third picture shows LDL level, and the fourth picture shows abundances of miR-96 and miR-185, chow represents the group of normal diet fed mice, HFD represents the group of high fat diet fed mice. *P<0.05, **P<0.01, in comparison to ctl-miR.

After ApoE knockout mice are fed on high-fat diet for 8 weeks, the total cholesterol level and LDL cholesterol level in serum significantly increase, and the expression of miR-96 and miR-185 significantly decrease in hepatocytes, and the expression level of SR-BI significantly increase (As shown in FIG. 17).

5.4 Effects of miR-96, miR-185 and miR-223 on the mRNA Level of SR-BI in Macrophage and Dil-HDL Uptake.

Macrophage THP-1 induced by PMA for 24 hours is transiently transfected with miR-96, miR-185 or miR-223 using Lipofectamine RNAiMAX Transfection reagent (Invitrogen), and after 72 hours, The mRNA level of SR-BI is detected by real-time RT-PCR, or Dil-HDL uptake by macrophage is detected by flow cytometry after incubation of the transfected macrophage with 2 µg/ml Dil-HDL for 4 hours.

Figure 18:
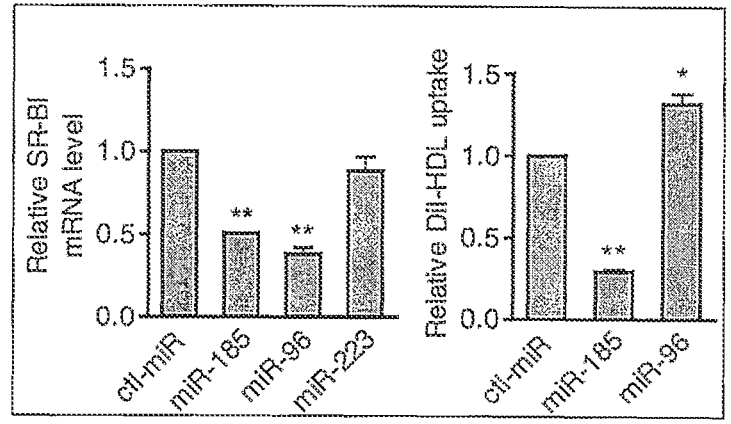
FIG. 18 shows effects of miR-96, miR-185 and miR-223 on the mRNA level of SR-BI and Dil-HDL uptake in macrophage, where ctl-miR represents miRNA control, chow represents the group of normal diet, and HFD represents the group of high-fat diet. *P<0.05, **P<0.01, n=6 (chow) and n=5 (HFD).

From experimental results, it is shown that the mRNA level of SR-BI in macrophage is down-regulated after transfection with miR-96, miR-185 and miR-223. The Dil-HDL uptake significantly decreases after transfection with miR-185, while the uptake of Dil-HDL significantly increases after transfection with miR-96 (as shown in FIG. 18).

Although the specific models for carrying out the invention have been described in detail, those skilled in the art will understand these details can be modified and changed according to all teachings in the art, and these changes are within the protection scope of the invention. The whole scope of the invention is given by the attached claims and any equivalents thereof.

What is claimed is:

1. A method for treating a disease related to lipid metabolism, comprising the step of administering an effective amount of an antisense RNA of a microRNA to a subject in need of treating said disease, wherein the microRNA is one or two or three miRNAs selected from the group consisting of miRNA-96, miRNA-185 and miRNA-223, and wherein the disease related to lipid metabolism is atherosclerosis or a cardiovascular disease, and the miRNA-185 has a sequence as set forth in SEQ ID NO:2.

2. The method according to claim 1, wherein said cardiovascular disease is coronary heart disease or myocardial infarction.

3. The method according to claim 1, wherein the antisense RNA of miRNA-185 has a sequence as set forth in SEQ ID NO:5.

4. The method according to claim 1, wherein the subject is human.

5. A method for improving the level of high density lipoprotein (HDL) in a mammal and/or reducing the level of low density lipoprotein (LDL), cholesterol or triglyceride in blood in a mammal, which comprises the step of administering an effective amount of an antisense RNA of a microRNA to a mammal in need of improving the level of high density lipoprotein (HDL) and/or reducing the level of low density lipoprotein (LDL), cholesterol or triglyceride, wherein the microRNA is one or two or three miRNAs selected from the group consisting of miRNA-96, miRNA-185, and miRNA-223, and the miRNA-185 has a sequence as set forth in SEQ ID NO:2.

6. The method according to claim 5, wherein the antisense RNA of miRNA-185 has a sequence as set forth in SEQ ID NO:5.

7. The method according to claim 5, wherein the mammal is human.

* * * * *